United States Patent
Chien

(10) Patent No.: US 9,952,451 B2
(45) Date of Patent: Apr. 24, 2018

(54) COLORANT FILM, METHOD FOR MAKING COLORANT FILM, AND OPHTHALMIC LENS

(71) Applicant: HON HAI PRECISION INDUSTRY CO., LTD., New Taipei (TW)

(72) Inventor: Hsiu-Wen Chien, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 215 days.

(21) Appl. No.: 14/961,092

(22) Filed: Dec. 7, 2015

(65) Prior Publication Data
US 2017/0123235 A1    May 4, 2017

(30) Foreign Application Priority Data

Oct. 30, 2015 (TW) .............................. 104135944 A

(51) Int. Cl.
| | |
|---|---|
| G02C 7/04 | (2006.01) |
| G02C 7/10 | (2006.01) |
| A61L 27/26 | (2006.01) |
| A61L 27/52 | (2006.01) |
| A61L 27/54 | (2006.01) |
| A61L 27/58 | (2006.01) |

(Continued)

(52) U.S. Cl.
CPC .............. *G02C 7/108* (2013.01); *A61L 27/26* (2013.01); *A61L 27/52* (2013.01); *A61L 27/54* (2013.01); *A61L 27/58* (2013.01); *B29C 35/0805* (2013.01); *B29C 41/003* (2013.01); *B29C 41/02* (2013.01); *B29C 41/22* (2013.01); *B29C 41/46* (2013.01); *B29D 11/00* (2013.01); *B29D 11/00038* (2013.01); *B29D 11/00903* (2013.01); *C08J 3/24* (2013.01); *C08J 3/241* (2013.01); *C08J 3/28* (2013.01); *C08J 5/18* (2013.01); *G02C 7/049* (2013.01); *A61L 2300/11* (2013.01); *A61L 2300/62* (2013.01); *B29C 2035/0827* (2013.01); *B29K 2105/0002* (2013.01); *B29K 2105/0005* (2013.01); *B29K 2105/0032* (2013.01); *B29K 2105/0061* (2013.01); *B29K 2105/0076* (2013.01); *B29K 2995/002* (2013.01); *B29L 2011/0041* (2013.01); *C08J 2333/14* (2013.01); *G02C 7/046* (2013.01); *G02C 2202/16* (2013.01)

(58) Field of Classification Search
CPC .... G02C 7/046; G02C 7/049; G02C 2202/16; A61L 2300/11; A61L 2300/622; B29K 2995/002; B29L 2011/0041
USPC .............. 428/321.5; 351/159.24, 159.78, 162
See application file for complete search history.

(56) References Cited

U.S. PATENT DOCUMENTS

| | | | |
|---|---|---|---|
| 9,175,153 B2 * | 11/2015 | Trexler | ...................... C08L 1/02 |
| 2005/0031847 A1 * | 2/2005 | Martens | ............... A61K 8/0208 |
| | | | 428/321.5 |
| 2011/0236491 A1 * | 9/2011 | Chantalat | ............. A61K 8/0287 |
| | | | 424/490 |

\* cited by examiner

*Primary Examiner* — Bruce H Hess
(74) *Attorney, Agent, or Firm* — ScienBiziP, P.C.

(57) ABSTRACT

A method for making a colorant film providing eye care includes following steps of providing a plurality of microcapsules containing hydrogen peroxide aqueous solution; mixing a hydrophilic monomer, a cross-linking agent, and an initiator to form a mixture; mixing the microcapsules, the mixture, a pigment, and a solvent to form a colorant material; printing the colorant material into a mold; and heating or irradiating the colorant material in the mold to copolymerize the hydrophilic monomer, the initiator, and the cross-linking agent. A colorant film, and the manufacture of an ophthalmic lens are also provided.

15 Claims, 4 Drawing Sheets

(51) Int. Cl.
  *B29C 35/08* (2006.01)
  *B29C 41/00* (2006.01)
  *B29C 41/02* (2006.01)
  *B29C 41/22* (2006.01)
  *B29C 41/46* (2006.01)
  *C08J 3/24* (2006.01)
  *C08J 3/28* (2006.01)
  *C08J 5/18* (2006.01)
  *B29D 11/00* (2006.01)
  *B29K 105/00* (2006.01)
  *B29L 11/00* (2006.01)

COLORANT FILM, METHOD FOR MAKING COLORANT FILM, AND OPHTHALMIC LENS

FIELD

The subject matter herein generally relates to eye care.

BACKGROUND

People who do not have good eyesight use ophthalmic lens to improve their eyesight.

BRIEF DESCRIPTION OF THE DRAWINGS

Implementations of the present technology will now be described, by way of example only, with reference to the attached figures.

DETAILED DESCRIPTION

Figure 1:
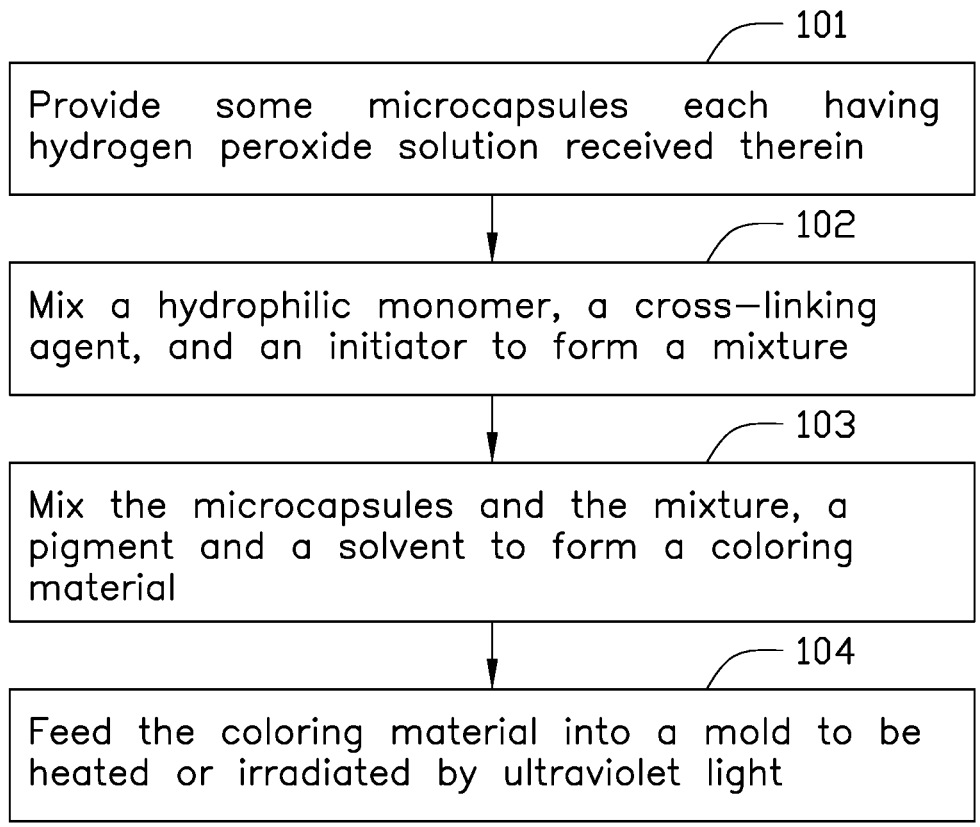
FIG. 1 is a flowchart of an embodiment of a method for making a colorant film.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The term "comprising," when utilized, means "including, but not necessarily limited to"; it specifically indicates open-ended inclusion or membership in the so-described combination, group, series and the like.

FIG. 1 illustrates a flowchart of a method for making a colorant film in accordance with an exemplary embodiment. The exemplary method is provided by way of example, as there are a variety of ways to carry out the method. Each block shown in FIG. 1 represents one or more processes, methods, or subroutines, carried out in the exemplary method. Furthermore, the illustrated order of blocks is by example only and the order of the blocks can change. Additional blocks may be added or fewer blocks may be utilized, without departing from this disclosure. The exemplary method can begin at block 101.

At block 101, a plurality of microcapsules each containing hydrogen peroxide aqueous solution are provided. The hydrogen peroxide aqueous solution has a mass concentration of about 0.5% to about 8%.

Each microcapsule has a peripheral wall. The peripheral wall of each microcapsule is made of a material selected from a group consisting of natural macromolecular material, semisynthetic macromolecular material, and synthetic macromolecular material. The natural macromolecular material may be selected from a group consisting of gelatin, chitin, starch, arabic gum, shellac, dextrin, wax, pine resin, sodium alginate, and zein. The semisynthetic macromolecular material may be selected from a group consisting of carboxymethyl cellulose (CMC), methyl cellulose, and ethyl cellulose. The synthetic macromolecular material may be selected from a group consisting of poly(lactic-co-glycolic acid) (PLGA), polylactic acid (PLA), and polyglycolide acid (PGA).

The microcapsules containing hydrogen peroxide aqueous solution may be made by a known method used in the field, such as simple coacervation process, complex coacervation process, solvent-nonsolvent process, in-liquid drying process, interface polycondensation process, radiation and cross-linking process, spray drying process, spray congealing process, suspension coating process, multiorfice-centrifugal process, or pan coating process.

At block 102, a mixture is formed by mixing a hydrophilic monomer, a cross-linking agent, and an initiator. The hydrophilic monomer has a mass percentage of about 63% to about 85% in the mixture. The cross-linking agent has a mass percentage of about 5% to about 34% in the mixture. The initiator has a mass percentage of about 3% to about 10% in the mixture.

The hydrophilic monomer may be selected from methacrylate compounds and/or acrylate compounds, such as 2-hydroxyethyl methacrylate (HEMA), methyl methacrylate (MMA), poly(dimethylsiloxane), 3-methacryloxypropyletris(trimethylsiloxy)silane, N-vinyl pyrrolidone (NVP), glycidyl methacrylate, N,N-dimethylacrylamide, and methyl acrylate (MA), or any combination thereof.

The cross-linking agent may be selected from a group consisting of ethylene glycol dimethacrylate (EGDMA) and trimethylolpropane trimethacrylate (TMPTMA). The initiator may be selected from a group consisting of azodiisobutyrodinitrile (AIBN), and a clear liquid under the trade name "Irgacure-1173" available commercially from Chemical Industries Basel (CIBA) Corporation.

At block 103, a pigment, a solvent, the microcapsules, and the mixture are mixed to form a colorant material. The pigment may be FD&C pigment which be certificated by United States Food and Drug Administration (FDA), such as FD&C yellow 5, FD&C yellow 6, FD&C red 3, FD&C red 40, FD&C blue 1, and FD&C blue 2, or any combination thereof. The solvent may be selected from a group consisting of toluene and methanol. In at least one embodiment, the microcapsules have a mass percentage of about 0.01% to about 7% in the colorant material. The mixture has a mass percentage of about 31% to about 74.99% in the colorant material. The pigment has a mass percentage of about 20% to about 41% in the colorant material. The solvent has a mass percentage of about 5% to about 21% in the colorant material.

At block 104, the colorant material is printed into a mold and is heated or irradiated by ultraviolet light, causing the hydrophilic monomer, the initiator, and the cross-linking agent to copolymerize to form the colorant film. In at least one embodiment, the colorant film has a thickness of about 1 μm to about 45 μm. The heating or the ultraviolet irradiation of the colorant material in the mold may last for about 10 seconds to about 3 minutes.

The peripheral walls of the microcapsules will slowly decompose by reacting with the secretions of eyes and the hydrogen peroxide will be released from the microcapsules. The released hydrogen peroxide can chemically decompose into oxygen gas under light irradiation. When the mass concentration of the hydrogen peroxide aqueous solution received in the microcapsule is greater than 8%, the eyes would be corroded by the hydrogen peroxide aqueous solution. When the mass concentration of the hydrogen peroxide aqueous solution received in the microcapsule is less than 0.5%, the hydrogen peroxide aqueous solution may be unable to produce enough oxygen gas.

Example 1

A mixture was formed by mixing 2-hydroxyethyl methacrylate, ethylene glycol dimethacrylate, and Irgacure-1173. The 2-hydroxyethyl methacrylate had a mass percentage of 65% in the mixture. The ethylene glycol dimethacrylate had a mass percentage of 25% in the mixture. Irgacure-1173 had a mass percentage of 10% in the mixture. A colorant material was formed by mixing the microcapsules containing hydrogen peroxide aqueous solution, FD&C blue 1, toluene, and the mixture. The microcapsules having a mass concentration of 0.5% had a mass percentage of 0.05% in the colorant material. The material of the peripheral walls of the microcapsules was chitin. FD&C blue 1 had a mass percentage of 23% in the colorant material. The toluene had a mass percentage of 19% in the colorant material. The mixture had a mass percentage of 57.95% in the colorant material. The material was printed into a mold and was irradiated by ultraviolet light for 30 seconds, thereby forming a colorant film.

Example 2

A mixture was formed by mixing 2-hydroxyethyl methacrylate, ethylene glycol dimethacrylate, and Irgacure-1173. The 2-hydroxyethyl methacrylate had a mass percentage of 67.5% in the mixture. The ethylene glycol dimethacrylate had a mass percentage of 28% in the mixture. Irgacure-1173 had a mass percentage of 4.5% in the mixture. A colorant material was formed by mixing a plurality of microcapsules containing hydrogen peroxide aqueous solution, FD&C red 40, FD&C blue 1, methanol, and the mixture. The microcapsules having a mass concentration of 0.8% had a mass percentage of 5% in the colorant material. The material of peripheral walls of the microcapsules is poly(lactic-co-glycolic acid). FD&C red 40 had a mass percentage of 10.8% in the colorant material. FD&C blue 1 had a mass percentage of 15.4% in the colorant material. The toluene had a mass percentage of 21% in the colorant material. The mixture had a mass percentage of 45.8% in the colorant material. The colorant material was printed into a mold and was irradiated by ultraviolet light for 30 seconds, thereby forming a colorant film.

A colorant material used in the method to make the colorant film is provided herein. The colorant material comprises a plurality of microcapsules containing hydrogen peroxide aqueous solution, a pigment, a solvent, and a mixture formed by mixing a hydrophilic monomer, a cross-linking agent, and an initiator. In at least one embodiment, the microcapsules have a mass percentage of about 0.01% to about 7% in the colorant material. The pigment has a mass percentage of about 20% to about 41% in the colorant material. The solvent has a mass percentage of about 5% to about 21% in the colorant material. The mixture has a mass percentage of about 31% to about 74.99% in the colorant material. The hydrophilic monomer has a mass percentage of about 63% to about 85% in the mixture. The cross-linking agent has a mass percentage of about 5% to about 34% in the mixture. The initiator has a mass percentage of about 3% to about 10% in the mixture. When the colorant material is heated or irradiated by ultraviolet light, the hydrophilic monomer, the initiator, and the cross-linking agent copolymerize to form the colorant film.

Figure 2:
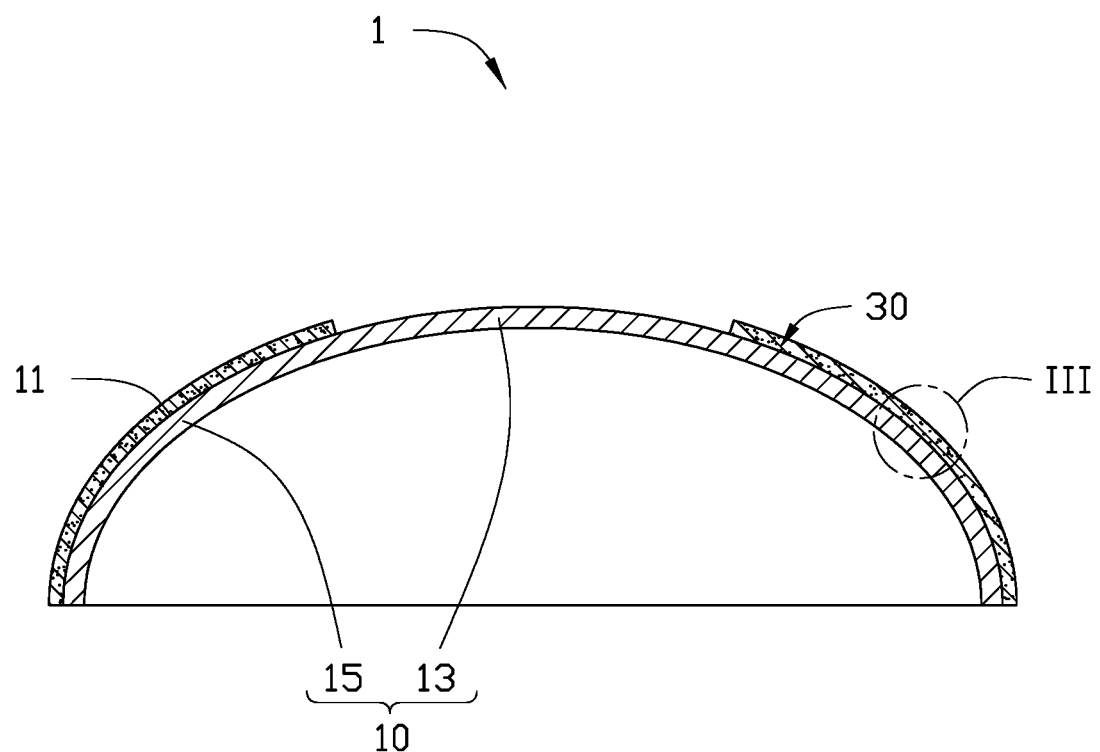
FIG. 2 is a cross-sectional view of an embodiment of an ophthalmic lens.
Figure 3:
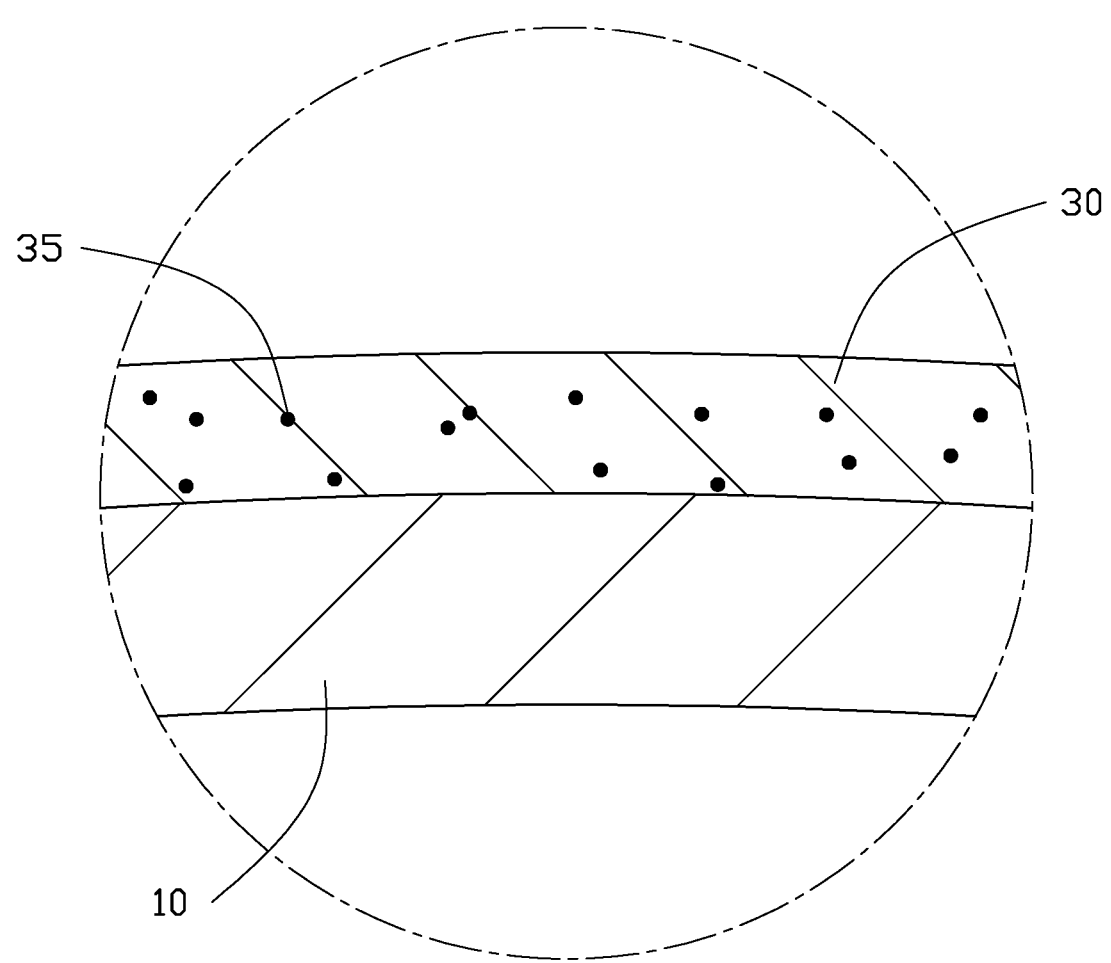
FIG. 3 shows an enlarged cross section of circled portion III of FIG. 2.

FIG. 2 illustrates an embodiment of an ophthalmic lens 1. The ophthalmic lens 1 comprises a substrate 10 and a colorant film 30 attached to a surface 11 of the substrate 10. The substrate 10 may be made of hydrogel or silicone hydrogel. The substrate 10 comprises a non-opaque pupil region 13 and a generally annular-shaped iris region 15 surrounding the non-opaque pupil region 13. The colorant film 30 covers the generally annular-shaped iris region 15. FIG. 3 illustrates a partial enlarged cross section of the ophthalmic lens 1. The colorant film 30 comprises a plurality of microcapsules 35 containing hydrogen peroxide aqueous solution, the pigment and a matrix copolymerized from the hydrophilic monomer, the cross-linking agent, and the initiator. The microcapsules 35 and the pigment are dispersed in the matrix. The colorant film 30 may have a thickness of about 1 µm to about 45 µm. The colorant film 30 made by the above-described method in included in at least one embodiment of manufacturing the ophthalmic lens 1. After the colorant film 30 is formed in the mold, material for forming the substrate 10 is added into the mold, and then is irradiated by ultraviolet light to form the substrate 10, thereby attaching the colorant film 30 to the surface 11 of the substrate 10. In another embodiment of manufacturing the ophthalmic lens 1, the colorant film 30 is made by applying the colorant material on the surface 11 of the substrate 10 and heating or irradiating the same by ultraviolet light. During use of the ophthalmic lens 1, the peripheral walls of the microcapsules 35 decompose slowly by reacting with the secretions of eyes and hydrogen peroxide is released from the microcapsules 35. The released hydrogen peroxide chemically decomposes into oxygen gas under light. The substrate 10 being made of hydrogel or silicone hydrogel with oxygen permeability, the produced oxygen gas can pass through the substrate 10 and reach the eyes, thereby preventing eyes from discomfort.

Figure 4:
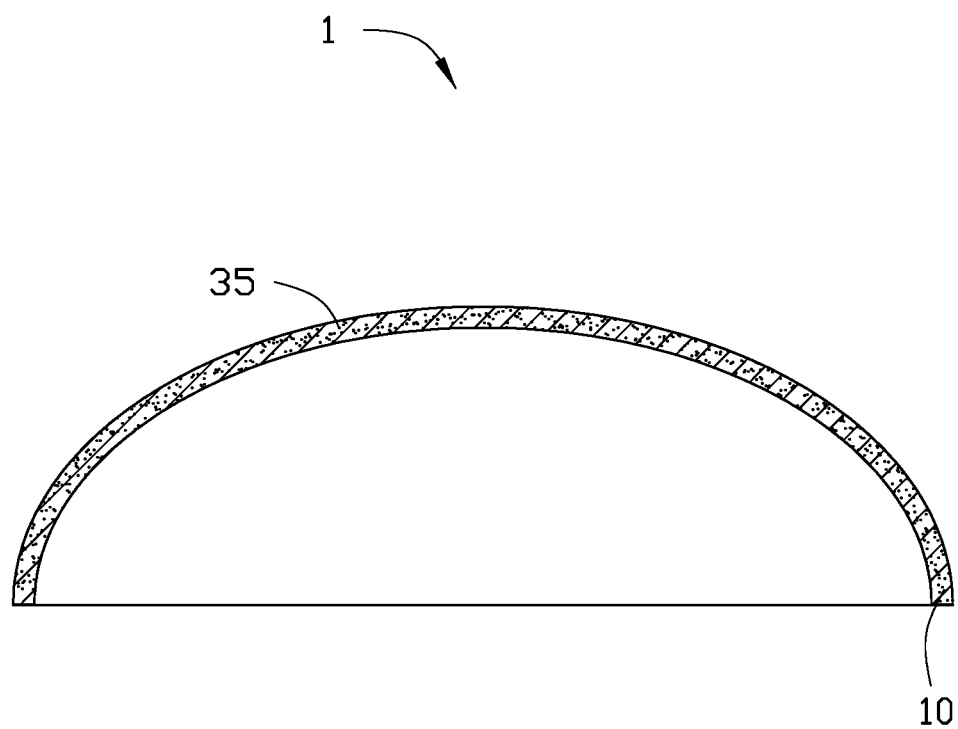
FIG. 4 shows a cross-sectional view of another embodiment of an ophthalmic lens.

FIG. 4 illustrates a second embodiment of an ophthalmic lens 1, the microcapsules 35 containing hydrogen peroxide aqueous solution are dispersed in the substrate 10 to form the ophthalmic lens 1.

It is to be understood, even though information and advantages of the present embodiments have been set forth in the foregoing description, together with details of the structures and functions of the present embodiments, the disclosure is illustrative only; changes may be made in detail, especially in matters of shape, size, and arrangement of parts within the principles of the present embodiments to the full extent indicated by the plain meaning of the terms in which the appended claims are expressed.

What is claimed is:
1. A method for making a colorant film comprising:
providing a plurality of microcapsules containing hydrogen peroxide aqueous solution;
mixing a hydrophilic monomer, a cross-linking agent, and an initiator together to form a mixture;
mixing the microcapsules, the mixture, a pigment and a solvent together to form a colorant material;
printing the colorant material into a mold; and
heating the colorant material in the mold or irradiating the colorant material in the mold by ultraviolet light to copolymerize the hydrophilic monomer, the initiator, and the cross-linking agent.

2. The method of claim 1, wherein the microcapsules have a mass percentage of about 0.01% to about 7% in the colorant material, the mixture has a mass percentage of about 31% to about 74.99% in the colorant material, the pigment has a mass percentage of about 20% to about 41% in the colorant material, the solvent has a mass percentage of about 5% to about 21% in the colorant material.

3. The method of claim 1, wherein each of the microcapsules has a peripheral wall made of a material selected from a group consisting of natural macromolecular material, semisynthetic macromolecular material, and synthetic macromolecular material.

4. The method of claim 3, wherein the natural macromolecular material is selected from a group consisting of gelatin, chitin, starch, arabic gum, shellac, dextrin, wax, pine resin, sodium alginate, and zein; the semisynthetic macromolecular material is selected from a group consisting of carboxymethyl cellulose, methyl cellulose, and ethyl cellulose; the synthetic macromolecular material is selected from a group consisting of poly(lactic-co-glycolic acid), polylactic acid, and polyglycolide acid.

5. The method of claim 1, wherein the hydrogen peroxide aqueous solution has a mass concentration of 0.5% to 8%.

6. A colorant film comprising:
   a matrix copolymerized from a hydrophilic monomer, an initiator, and a cross-linking agent;
   a pigment; and
      a plurality of microcapsules containing hydrogen peroxide aqueous solution;
   wherein the pigment and the microcapsules are dispersed in the matrix.

7. The colorant film of claim 6, wherein the colorant film is formed by heating or by irradiating a colorant material by ultraviolet light; the colorant material comprises the pigment, the microcapsules, a mixture comprising the hydrophilic monomer, the initiator, and the cross-linking agent, and a solvent; the microcapsules have a mass percentage of about 0.01% to about 7% in the colorant material, the mixture has a mass percentage of about 31% to about 74.99% in the colorant material, the pigment has a mass percentage of about 20% to about 41% in the colorant material, and the solvent has a mass percentage of about 5% to about 21% in the colorant material.

8. The colorant film of claim 6, wherein each of the microcapsules has a peripheral wall made of a material selected from a group consisting of natural macromolecular material, semisynthetic macromolecular material, and synthetic macromolecular material.

9. The colorant film of claim 8, wherein the natural macromolecular material is selected from a group consisting of gelatin, chitin, starch, arabic gum, shellac, dextrin, wax, pine resin, sodium alginate, and zein; the semisynthetic macromolecular material is selected from a group consisting of carboxymethyl cellulose, methyl cellulose, and ethyl cellulose; the synthetic macromolecular material is selected from a group consisting of poly(lactic-co-glycolic acid), polylactic acid, and polyglycolide acid.

10. The colorant film of claim 6, wherein the colorant film has a thickness of 1 µm to 45 µm, the hydrogen peroxide aqueous solution has a mass concentration of 0.5% to 8%.

11. An ophthalmic lens comprising:
   a substrate made of a hydrogel or silicone hydrogel; and
   a colorant film attached to a surface of the substrate;
   wherein the colorant film comprises a plurality of microcapsules containing hydrogen peroxide aqueous solution, the colorant film further comprises a matrix copolymerized from a hydrophilic monomer, an initiator, and a cross-linking agent, the microcapsules are dispersed in the matrix.

12. The ophthalmic lens of claim 11, wherein each of the microcapsules has a peripheral wall made of a material selected from a group consisting of natural macromolecular material, semisynthetic macromolecular material, and synthetic macromolecular material.

13. The ophthalmic lens of claim 12, wherein the natural macromolecular material is selected from a group consisting of gelatin, chitin, starch, arabic gum, shellac, dextrin, wax, pine resin, sodium alginate, and zein; the semisynthetic macromolecular material is selected from a group consisting of carboxymethyl cellulose, methyl cellulose, and ethyl cellulose; the synthetic macromolecular material is selected from a group consisting of poly(lactic-co-glycolic acid), polylactic acid, and polyglycolide acid.

14. The ophthalmic lens of claim 11, wherein the hydrogen peroxide aqueous solution has a mass concentration of 0.5% to 8%.

15. The ophthalmic lens of claim 11, wherein the colorant film has a thickness of 1 µm to 45 µm.

* * * * *